(12) United States Patent
Denyer et al.

(10) Patent No.: US 12,318,582 B1
(45) Date of Patent: Jun. 3, 2025

(54) MEDICAMENT DELIVERY DEVICE

(71) Applicant: Genzyme Corporation, Cambridge, MA (US)

(72) Inventors: Timothy Denyer, Melbourn (GB); James Bradford, Melbourn (GB); Alexander Hee-Hanson, Melbourn (GB); Robert Wilson, Melbourn (GB); Dean Twite, Melbourn (GB); Thomas Lever, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/818,944

(22) Filed: Aug. 29, 2024

(51) Int. Cl.
*A61M 5/32* (2006.01)
*A61M 5/20* (2006.01)

(52) U.S. Cl.
CPC ........ *A61M 5/2033* (2013.01); *A61M 5/3204* (2013.01); *A61M 2005/3267* (2013.01)

(58) Field of Classification Search
CPC ........ A61M 5/3204; A61M 2005/3267; A61M 5/326; A61M 5/3202; A61M 2005/3247; A61M 5/3243
See application file for complete search history.

(56) References Cited

U.S. PATENT DOCUMENTS

| | | | |
|---|---|---|---|
| 4,118,611 A | 10/1978 | Harris | |
| 5,609,577 A | 3/1997 | Haber et al. | |
| 5,743,888 A | 4/1998 | Wilkes et al. | |
| 6,261,264 B1 | 7/2001 | Tamaro | |
| 10,765,811 B2 | 9/2020 | Vedrine et al. | |
| 10,926,040 B2 | 2/2021 | Karasawa | |
| 2004/0044318 A1 | 3/2004 | Fiser et al. | |
| 2005/0171477 A1* | 8/2005 | Rubin | A61M 5/2033 604/156 |
| 2011/0276029 A1 | 11/2011 | Field | |
| 2012/0101475 A1* | 4/2012 | Wilmot | A61M 5/2033 604/506 |

(Continued)

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

(Continued)

*Primary Examiner* — Courtney B Fredrickson
(74) *Attorney, Agent, or Firm* — Fish & Richardson P.C.

(57) ABSTRACT

The present disclosure relates to a medicament delivery device comprising a housing, a needle, a needle cover, a needle cover biasing member, a drive mechanism, and a needle cover extension mechanism. The needle cover is axially movable between an extended position and a retracted position. The needle cover biasing member is configured to bias the needle cover axially in the distal direction towards the extended position. The needle cover extension mechanism comprises a second biasing member and a release element. The second biasing member is configured to bias the needle cover into its extended position post-use of the device. The release element has a first state configured to prevent the second biasing member from biasing the needle cover into the extended position and a second state configured to allow the second biasing member to bias the needle cover into the extended position.

20 Claims, 6 Drawing Sheets

(56) References Cited

U.S. PATENT DOCUMENTS

| | | |
|---|---|---|
| 2016/0271319 A1 | 9/2016 | Bengtsson et al. |
| 2018/0200487 A1 | 7/2018 | Sokolski et al. |
| 2022/0288318 A1 | 9/2022 | Plambech et al. |
| 2024/0198013 A1 | 6/2024 | Laurence et al. |

OTHER PUBLICATIONS

Speciale et al., "Snap-Through Buckling Mechanism for Frequency-up Conversion in Piezoelectric Energy Harvesting," Applied Sciences, May 23, 2020, 10(10):3614, 18 pages.
U.S. Appl. No. 18/819,383, filed Aug. 29, 2024, Timothy Denyer.
U.S. Appl. No. 18/819,625, filed Aug. 29, 2024, Timothy Denyer.
U.S. Appl. No. 18/819,704, filed Aug. 29, 2024, Timothy Denyer.

\* cited by examiner

MEDICAMENT DELIVERY DEVICE

TECHNICAL FIELD

This application relates to a medicament delivery device.

BACKGROUND

Medicament delivery devices are used to deliver a range of medicaments.

In some devices, the device must be held in a holding position at an injection site for a predetermined period of time, to ensure that the correct dose of medicament is dispensed from the device, before removing the device from the injection site.

It may be difficult to hold the device in the holding position whilst the medicament is dispensed. This may result in pain, discomfort, a wet injection site, early device removal and/or partial delivery of the medicament.

The present disclosure provides an improved medicament delivery device.

SUMMARY

According to a first aspect of the present disclosure, there is provided a medicament delivery device comprising a housing comprising a proximal end and a distal end, a needle and a needle cover, wherein the needle cover is axially movable between an extended position, in which the needle cover extends from the distal end of the housing and covers a distal end of the needle, and a retracted position, in which the needle cover is located in a proximal position relative to the extended position such that the needle protrudes from a distal end of the needle cover, a needle cover biasing member configured to bias the needle cover axially in the distal direction towards the extended position, a drive mechanism comprising a drive member, and a plunger rod configured to move from a proximal position to a distal position under the force of the drive member; and a needle cover extension mechanism comprising a second biasing member configured to bias the needle cover into its extended position post-use of the device, and a release element having a first state configured to prevent the second biasing member from biasing the needle cover into the extended position and a second state configured to allow the second biasing member to bias the needle cover into the extended position, wherein the release element is in the second state when the plunger rod is in a distal position.

One advantage of the techniques described in the present disclosure is that the biasing force of the needle cover biasing member can be reduced. Thus, the force required to be applied by an operator to activate and hold the medicament delivery device can be reduced. Thus, those who have difficulty with maintaining a high hold force throughout the injection duration will find using the medicament delivery device described in the present disclosure easier to hold. Furthermore, the use of the needle cover extension mechanism allows for a robust extension of the needle cover after use in order to provide protection against accidental contact with the used needle.

In some embodiments, the release element may be rotatable from the first state to the second state when the plunger is moved into the distal position.

Thus, by utilising rotation to move the release element from the first state to the second state, the medicament delivery device can be more compact as there is no need to accommodate space between other components for axial movement of the release element.

In some embodiments, the needle cover extension mechanism may further comprise a second biasing member holder and the release element may comprise an engaging portion, wherein the second biasing member holder may comprise a clip configured to engage with the engaging portion of the release element when the release element is in the first state and to be disengaged with the engaging portion of the release element when the release element is in the second state.

The second biasing member holder may provide a surface for the second biasing member to act upon. The second biasing member holder may also house or contain the second biasing member in order to prevent accidental contact of the second biasing member with another feature of the medicament delivery device. Advantageously, engagement of the clip of the second biasing member is able to withstand the extension force of the second biasing member such that the second biasing member cannot extend whilst the release member is in the first state.

In some embodiments, the release element may comprise a slot through which the second biasing member holder extends in the first state, the release element may be configured to rotate relative to the second biasing member holder such that when the release element is in the first state an engaging surface of the clip engages with a proximal engaging surface of the release element and when the release element is in the second state the engaging surface of the clip is disengaged from the proximal engaging surface of the release element.

Thus, the timing of the release of the second biasing member holder and consequently the extension of the second biasing member can be accurately controlled. The release of the second biasing member can be automatically timed based on movement of the release element, which can be automated by interaction with other components of the medicament delivery device. Furthermore, the second biasing member does not need to be compressed further before it is released.

In some embodiments, the slot may extend arcuately in the release element.

The arcuate slot advantageously allows for rotation of the release member without the release element's movement being inhibited by contact between the arm of the second biasing member holder and the release member.

In some embodiments, the second biasing member may be located between a distal surface of the release element and a proximal facing surface of the second biasing member holder, the second biasing member may be configured to bias the second biasing member into contact with the needle cover to bias the needle cover into the extended position when the engaging surface of the clip aligns with the slot in the release member in the second state.

Thus, the biasing force of the second biasing member may act against the axially fixed release element causing the extension of the second biasing member to move the second biasing member holder distally, when released, and consequently extend the needle cover to prevent accidental contact with the needle. The distal located of the second biasing member also reduces the size of the second biasing member required.

In some embodiments, a distal end portion of the second biasing member holder may be configured to abut a distal end portion of the needle cover when the release element is in the second state and the second biasing member extends distally.

Thus, the second biasing member is always in contact with the distal end portion of second biasing member holder and so cannot accidentally contact another component of the medicament delivery device. This also removes the chance of a spring extending unevenly and not making contact with the needle cover. The contact between the second biasing member holder and needle cover even distributes the force of the second biasing member to move the needle cover parallel to the longitudinal axis of the medicament delivery device. Using the second biasing member holder ensures delivery of the force from the second biasing member to the needle cover.

In some embodiments the release element may comprise an annular flat plate.

Thus, the release element may take up minimal space within the medicament delivery device. In addition, the annular plate may allow for other components of the medicament delivery device to be moved axially through the release element.

In some embodiments, at least one of the needle cover biasing member and the second biasing member may be a coil spring.

In some embodiments, the release element may be rotationally coupled to the plunger rod, and the plunger rod may be rotatable between a first rotational position and a second rotational position when the plunger rod is in the distal position to move the release element from the first state into the second state.

Thus, the timing of the release of the second biasing member by the release element can be automatically controlled based on the movement of the plunger rod. Consequently, the addition of the needle cover biasing force can be automatically controlled, which takes an operational step away from the user. Furthermore, by coupling the release element to the plunger rod it can be ensured that the second biasing member is only released at the end of the plunger stroke.

In some embodiments, the plunger rod may comprise a slot having a first portion extending longitudinally, and the release element may comprise a protrusion located in the slot, the slot and protrusion being configured to allow relative axial movement between the plunger rod and the release element.

Thus, the plunger rod can be moved axially without movement of the second biasing member holder. This prevents premature contact between the second biasing member holder and the needle cover. Thus, there is no additional biasing force added to the needle cover during movement of the plunger rod.

In some embodiments, the protrusion of the release element may be located in the first portion of the slot when the plunger rod is in its proximal position and when the plunger rod is in its distal position.

Thus, the rotational position of the release element is fixed to the rotational position of the plunger rod for the whole of the plunger rod stroke. This means that the release element is only disengaged from the second biasing member holder at a predetermined position of the plunger rod.

In some embodiments, the drive mechanism may further comprise a drive member housing, the drive member housing may comprise a projection located in the slot of the plunger rod, wherein the projection may be located in the first portion of the slot for the majority of the plunger rod stroke from the proximal position such that the plunger rod is maintained in the first rotational position, and wherein the projection may be located in a second offset portion of the slot when the plunger rod is in the distal position such that the plunger rod is moved to the second rotational position.

Thus, movement of the plunger rod from the first rotational position to the second rotational position at the distal position of the plunger rod at the end of the plunger stroke can cause the release member to the second state and release the second biasing member to provide a force on the needle cover.

In some embodiments, the first and second portions of the slot may be connected by a third portion of the slot that extends helically about the plunger rod, wherein engagement between the projection of the drive member housing and the third portion of the slot may induce the plunger rod to rotate from its first rotational position to its second rotational position as the plunger rod is moved axially into its distal position.

In some embodiments, the projection of the drive member housing may be located proximally to the protrusion of the release element.

Thus, the projection of the drive member housing reaches the second portion of the slot first. Therefore, as the projection of the drive member housing causes the plunger rod to rotate, the protrusion of the release element in the first portion of the slot causes the release element to rotate with the plunger rod from the first state to the second state to disengage with the second biasing member holder to allow the second biasing member to extend distally.

In some embodiments, the drive mechanism may further comprise a rotating collar located at least partially within the drive member housing, the rotating collar may comprise a threaded surface, the plunger rod may comprise a threaded surface configured to cooperate with the threaded surface of the rotating collar, and the drive member may comprise a torsion spring.

Thus, the size of the drive mechanism can be reduced and located proximally. In addition, the rotational motion of the rotating collar can be transformed into axial motion of the plunger rod.

In some embodiments, the medicament delivery device may be configured to inject greater than 2 ml of medicament and/or wherein the medicament delivery device is configured to inject medicament having a viscosity of greater than 25 cP.

In some embodiments, the medicament delivery device may further comprise a needle cover lock configured to prevent proximal movement of the needle cover once the needle cover is in the extended position post-use.

Therefore, after use, the needle cover may permanently cover the needle to prevent an accidental contact with the used needle.

In some embodiments, the medicament delivery device may comprise medicament.

The medicament delivery device may comprise a container for containing the medicament. The medicament may be located in the container. The container may be a syringe. The syringe may comprise the needle. The container may be a cartridge which is initially separated form the needle when the needle cover is in the extended position.

According to a second aspect of the present disclosure, there is provided a method of moving a needle cover of a medicament delivery device to its extended position after use, the method comprising moving a plunger rod from a first rotational position to a second rotational position to move a release element from a first state, in which the release element prevents extension of a second biasing member, to a second state, in which the release element allows extension of a second biasing member, moving the needle cover under the biasing force of the second biasing member from the retracted position, in which a distal end of a needle protrudes from a distal end of the needle cover, to an extended position, in which the needle cover covers the distal end of the needle.

BRIEF DESCRIPTION OF THE FIGURES

Embodiments will now be described, by way of example only, with reference to the accompanying drawings, in which.

DETAILED DESCRIPTION

Figure 1A:
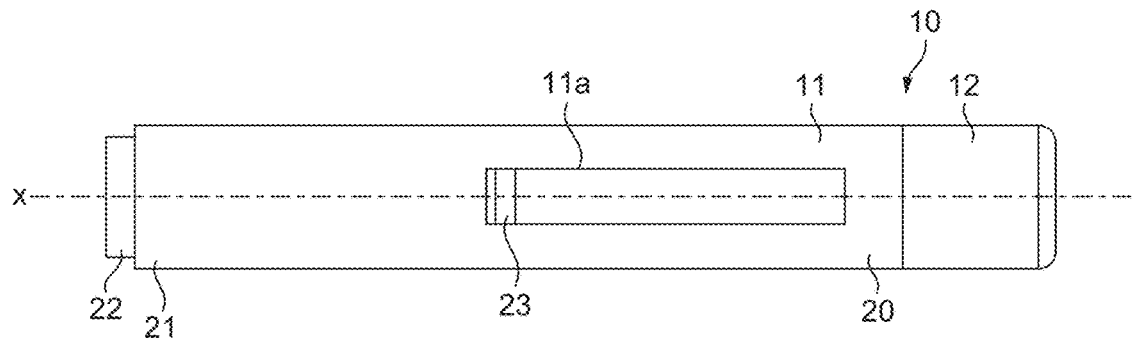
FIG. 1A shows an injector device with a cap attached.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component.

Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
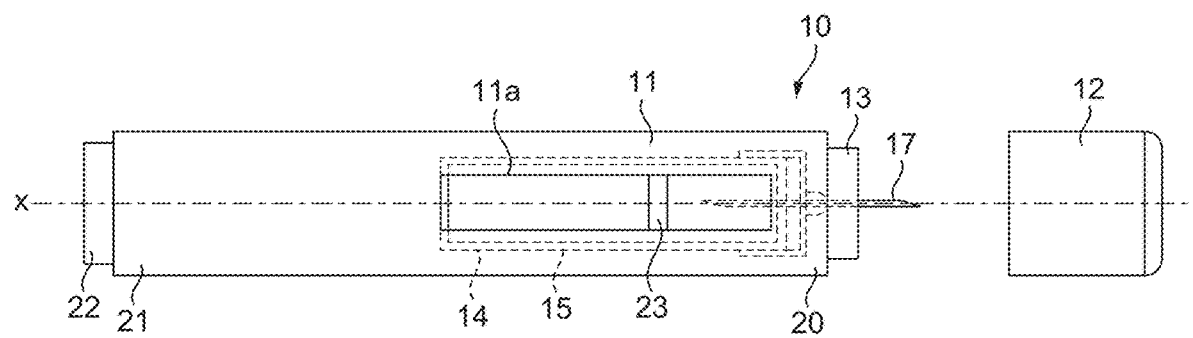
FIG. 1B shows the injector device of FIG. 1A with the cap removed.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23.

Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11. Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
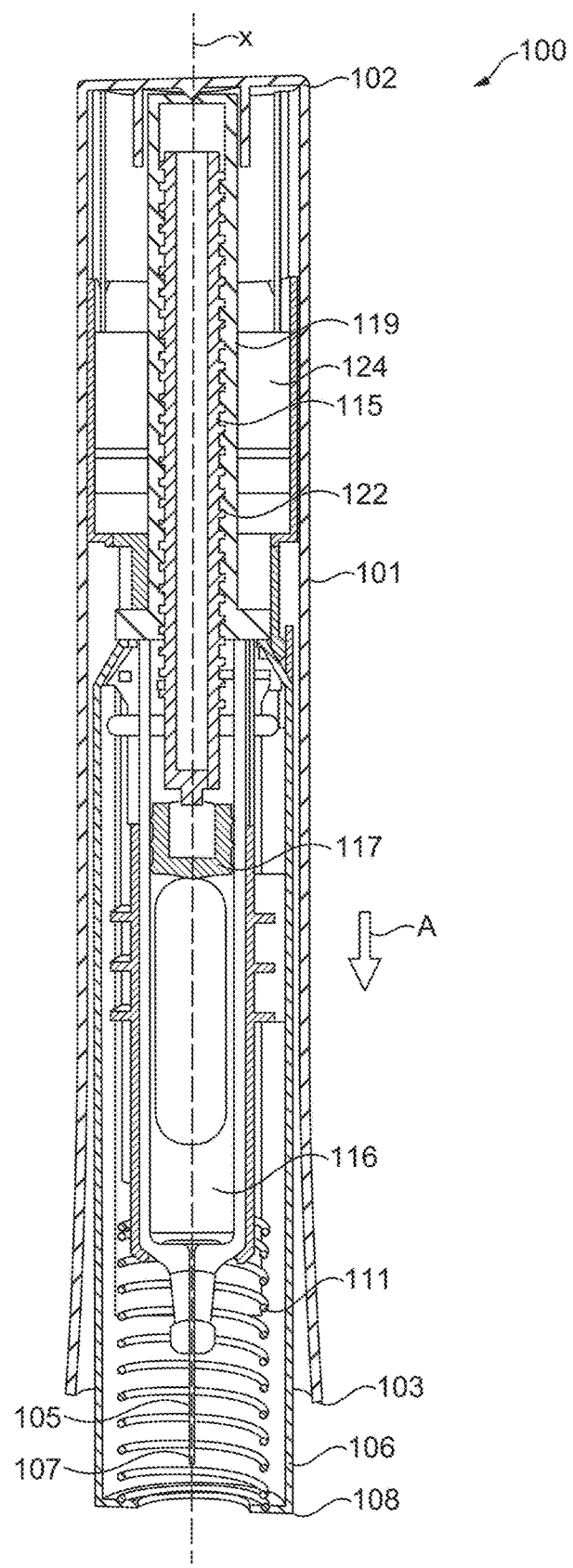
FIG. 2 shows a simplified schematic cross-sectional side view of a medicament delivery device.

FIG. 2 shows a simplified view of a medicament delivery device 100. The medicament delivery device 100 comprises a housing 101. The housing 101 comprises a proximal end 102 and a distal end 103. The medicament delivery device 101 further comprises a needle 105 for injecting medicament and a needle cover 106. The needle 105 has a distal end 107. The needle cover 106 is axially movable relative to the housing 101 between an extended position, in which the needle cover 106 extends from the distal end 103 of the housing 101 and covers the distal end 107 of the needle 105, and a retracted position, in which the needle cover 106 is located in a proximal position relative to the extend position such that the needle 105 protrudes from a distal end 108 of the needle cover 106 . . . . The medicament delivery device 100 extends along an axis X.

The medicament delivery device 100 is shown in the extended position in FIG. 2. The extended position may be the initial position in which the medicament delivery device 100 is provided.

The medicament delivery device 100 further comprises a needle cover biasing member 111. The needle cover biasing member 111 is configured to bias the needle cover 106 axially in the distal direction towards the extended position. The distal direction is indicated by the direction of the arrow A in FIG. 2. In some embodiments, the needle cover biasing member 111 may be a spring.

The medicament delivery device 100 may further comprise a plunger rod 115. The plunger rod 115 may be axially moveable within the housing 101. The medicament delivery device 100 may further comprise a syringe 116. The syringe 116 may be configured to contain medicament. The syringe 116 may comprise the needle 105 located on a distal end of the syringe 116. The plunger rod 115 may be axially movable within a syringe 116 of the medicament delivery device 100 to dispense medicament from the syringe 116 via the needle 105. The syringe 116 may comprise a piston 117. The plunger rod 115 may act on the piston to dispense medicament from the syringe 116 via the needle 105.

The medicament delivery device 100 may further comprise a collar 119. The collar 119 may be axially fixed relative to the housing 101. The collar 119 may interfaces with the plunger rod 115 via a screw thread 122. The medicament delivery device 100 may further comprise a drive member 124. The drive member 124 may be a biasing member that is configured to rotate the collar 119 when the drive member 124 is released. The drive member 124 may be a rotational biasing member, such as a spring. The spring 124 may be a torsion spring. The torsion spring 124 may be released when the needle cover 106 reaches a predetermined axial displacement in the proximal direction with a release mechanism (not shown). The rotation of the collar 119 may cause the plunger rod 115 to move distally within the syringe 116, in view of the screw thread 122, to thereby dispense medicament from the syringe 116 via the needle 105.

The needle cover 106 may be moved axially into the housing 101 uncovering the needle 105. The needle cover 106 may be moved proximally by being pressed against an injection site 125. The proximal axial displacement of the needle cover 106 may cause the release of the spring 124 which rotates the collar 119. The rotation of the collar 119 may move the plunger rod 115 axially in the distal direction within the syringe 116 to dispense the medicament via the needle 105.

The medicament delivery device 100 may be pressed against the injection site 125, to hold the needle cover 106 in the retracted position whilst the medicament is dispensed from the medicament delivery device 100. In known medicament delivery devices, the user must hold the medicament delivery device 100 against the injection site 125 against the force of the needle cover biasing member 111.

After the medicament has been dispensed, the medicament delivery device 100 is removed from the injection site 125. The needle cover 106 may move distally under the force of the needle cover biasing member 1111 to a locked position. In the locked position, the needle cover 106 covers the distal end 107 of the needle 105. In the locked position, the needle cover 106 may be prevented from moving proximally.

The medicament delivery device 100 may be configured to inject greater than 2 ml of medicament and/or the medicament delivery device 100 is configured to inject medicament having a viscosity of greater than 25 cP.

FIGS. 3A to 3D show a simplified schematic cross-sectional view of a medicament delivery device 200. The features described and/or contemplated in relation to the medicament delivery device 200 may be incorporated in the medicament delivery device 100 described and/or contemplated above. Furthermore, similar features and components will retain the same terminology and the reference numerals will be similar but having been increased in value by 100.

The medicament delivery device 200 comprises a housing 201. The housing 201 comprises a proximal end 202 and a distal end 203. The medicament delivery device 200 further comprises a needle 205 and a needle cover 206. The needle cover 206 is axially moveable between an extended position, shown in FIGS. 3A and 3D, and a retracted position, shown in FIGS. 3B and 3C.

In the extended position, the needle cover 206 extends from the distal end 203 of the housing 201. In the extended position, the needle cover 206 covers a distal end 207 of the needle 205. In the retracted position, the needle cover 205 is located in a proximal position relative to the extended position. In the retracted position, the needle 205 protrudes from a distal end 208 of the needle cover 206.

The medicament delivery device 200 further comprises a needle cover biasing member 211. The needle cover biasing member 211 is configured to bias the needle cover 206 in the distal direction towards the extended position.

The medicament delivery device 200 further comprises a drive mechanism 231. The drive mechanism 231 comprises a drive member 224 and a plunger rod 215. The plunger rod 215 is configured to move from a proximal position to a distal position. The drive member 224 is configured to bias the plunger rod 215 in the distal direction towards the distal position. Thus, the plunger rod 215 is configured to move from a proximal position to a distal position under the force of the drive member 224.

The medicament delivery device 200 further comprises a needle cover extension mechanism 241. The needle cover extension mechanism 241 may be a post-use mechanism. That is, the needle cover extension mechanism 241 may be operated once the medicament delivery device 200 has been used. The needle cover extension mechanism 241 comprises a second biasing member 242 and a release element 243.

The second biasing member 242 is configured to bias the needle cover into its extended position post-use of the medicament delivery device 200. The release element 243 has a first state and a second state. In the first state, the release element 243 is configured to prevent the second biasing member 242 from biasing the needle cover 206 into the extended position. In the second state, the release element 243 is configured to allow the second biasing member 242 to bias the needle cover 206 into the extended position.

One advantage of the techniques described in the present disclosure is that the biasing force of the needle cover biasing member 211 can be reduced. Thus, the force required to be applied by an operator to activate and hold the medicament delivery device 200 can be reduced. Thus, those who have difficulty with maintaining a high hold force throughout the injection duration will find using the medicament delivery device described in the present disclosure easier to hold. Furthermore, the use of the needle cover extension mechanism allows for a robust extension of the needle cover after use in order to provide protection against accidental contact with he used needle 205.

Figure 3A:
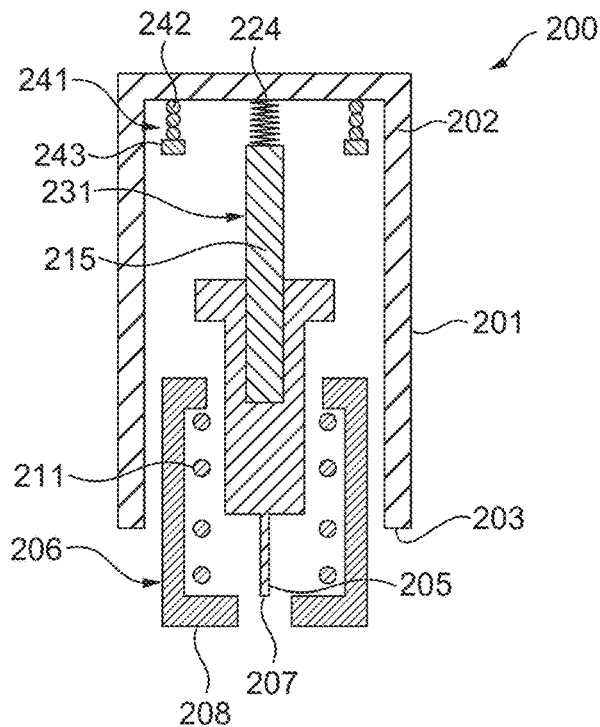
FIGS. 3A to 3D show simplified schematic cross-sectional side views of a medicament delivery device during various stages of operation.

Referring briefly to FIG. 3A, the medicament delivery device 200 is shown in its initial configuration. That is, the medicament delivery device 200 shown in FIG. 3A is in its configuration pre-use. The needle cover 206 may be in its extended position. The needle cover biasing member 211 may be in its extended state. That is, the needle cover biasing member 211 may be in its least compressed state. The plunger rod 215 may be in its proximal position. The drive member 224 may be in its first state. That is, the drive member 224 may be in a state where it has yet to be actuated or where it has the greatest potential energy. The release element 243 may be in its first state. That is, the release element may be configured to prevent the second biasing member 242 from extending. The second biasing member 242 may be in a state where it has yet to be actuated or where it has the greatest potential energy. It will be appreciated that the term "greatest potential energy" refers to a configuration of a component for use within the medicament delivery device which may not necessarily be the same as the overall state of potential energy achievable by said component.

As shown in FIG. 3A, the release element 243 may be located close to the proximal end 202 of the housing 201 of the medicament delivery device 200. In addition, the second biasing member 242 may be mounted on one end to the proximal end 202 of the housing 201. The other end of the second biasing member 242 may abut against a proximal facing surface of the release element 243 while the medicament delivery device 200 is in its initial configuration.

Figure 3B:
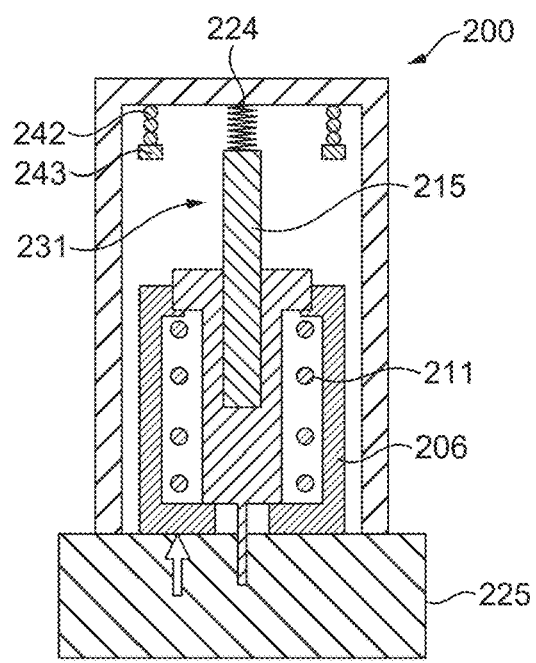

Referring to FIG. 3B, the medicament delivery device 200 is shown in its pre-injection configuration. That is, the medicament delivery device 200 has been moved from its initial configuration but has not dispensed medicament. The needle cover 206 may be in its retracted position. The needle cover biasing member 211 may be in its compressed state, i.e. its most compressed state during the operation of the medicament delivery device 200. The needle cover 206 may have been moved into its retracted state and the needle cover biasing member 211 into its compressed state by pushing the distal end of the medicament delivery device 200 against the injection site 225.

The plunger rod 215 may be in its proximal position. The drive member 224 may be in its first state. The release element 243 may be in its first state. The second biasing member 242 may be in in a state where it has yet to be actuated or where it has the greatest potential energy. That is, the plunger rod 215, drive member 224, release element 243, and second biasing member 242 may remain unchanged from the initial configuration.

It will be appreciated that in some embodiments, once the needle cover 206 reaches its retracted position, the needle cover 206 may trigger the drive mechanism 231. Alternatively, the drive mechanism 231 may be triggered manually by an operator of the medicament delivery device 200. Once the drive mechanism is actuated the drive member 224 may be configured to move the plunger rod 215 distally.

Figure 3C:
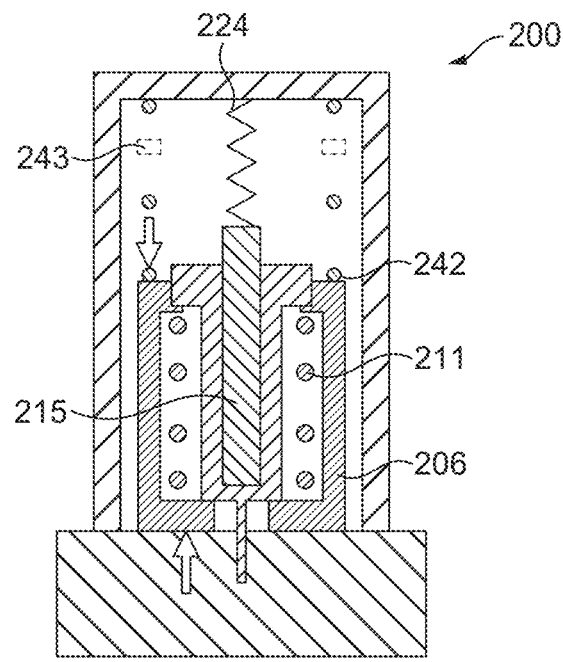

Referring to FIG. 3C, the medicament delivery device 200 is shown in its end of use configuration. That is, the medicament delivery device 200 is shown in FIG. 3C in its configuration after medicament has been dispensed. The needle cover 206 may be in its retracted position. The needle cover biasing member 211 may be in its compressed state.

The plunger rod 215 may be in its distal position. The drive member 224 may be in its second state. That is, the drive member 224 may be in a state where it has been actuated and fully deployed or where it has the least potential energy. It will be appreciated that the drive member 224 may have been fully deployed or occupy its lowest potential energy state within the operation of the medicament delivery device, and not necessarily deployed to fully or occupying its lowest overall potential energy state attainable outside the system, i.e. medicament delivery device. The plunger rod 215 may have been moved to its distal position under the force of the drive member 224.

The release element 243 may have been moved to its second state. The second state of the release element 243 is schematically represented by dashed in FIG. 3C by dashed lines in the location where the release element 243 was previously shown in FIG. 3A and FIG. 3B. The second biasing member 242 may be in its released state. That is, the second biasing member 242 may have been released in order to act on the needle cover 206. As shown in FIG. 3C, the second biasing member 242 may be in contact with the needle cover 206 once the release member is moved from its first state to its second state.

As shown in FIG. 3C, in some embodiments, one end of the second biasing member 242 may be configured to act directly on the needle cover 206. In some embodiments, one end of the second biasing member 242 may act directly on a proximal end of the needle cover 206.

Figure 3D:
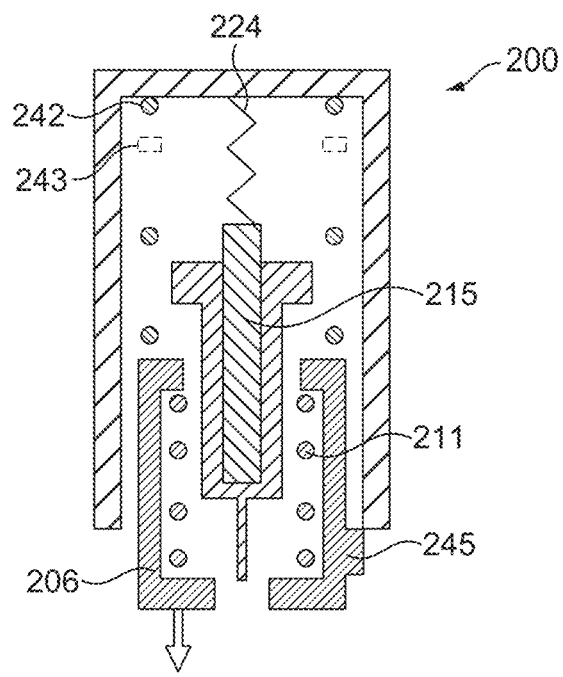

Referring briefly to FIG. 3D, the medicament delivery device 200 is shown in its final configuration. That is, the medicament delivery device 200 shown in FIG. 3D is in its configuration post-use after the medicament delivery device 200 has been removed from the injection site. The needle cover 206 may be in its extended position. The needle cover biasing member 211 may be in its extended state. That is, the needle cover biasing member 211 may be in its least compressed state.

The plunger rod 215 may be in its distal position. The drive member 224 may be in its second state. That is, the drive member 224 may be in a state where it has been actuated and fully deployed or where it has the least potential energy. The release element 243 may be in its second state.

The second biasing member 242 may be in its actuated state. That is, the second biasing member 242 may be in a state where it has been actuated and fully deployed or where it has the least potential energy. It will be appreciated that the second biasing member 242 may have been fully deployed or occupy its lowest potential energy state within the operation of the medicament deliver device, and not necessarily deployed to the fullest extend or lowest overall potential energy state that may be obtainable outside the system of the medicament delivery device 200.

In some embodiments, the medicament delivery device 200 may further comprise a needle cover lock 245. The needle cover lock 245 may be configured to prevent proximal movement of the needle cover once the needle cover 206 is in the extended position post-use. In some embodiments the needle cover lock 245 may comprise a projection 246 that extends from an outer surface of the needle cover 206. The projection 246 may be configured to abut against the distal end 203 of the housing 201 when the needle cover 206 is moved into its extended position post-use.

Referring now to FIGS. 4A to 5C, there is shown detailed schematic views of a medicament delivery device 300 according to the present disclosure. The features described and/or contemplated in relation to the medicament delivery device may be incorporated in the medicament delivery devices 100, 200 described and/or contemplated above. Furthermore, similar features and components will retain the same terminology and reference numerals will be similar but having been increased in value by 200 in relation to the features described with regards to the medicament delivery device 100 in FIG. 2 and by 100 in relation to the features described with regards to the medicament delivery device 200 in FIGS. 3A to 3D.

The medicament delivery device 300 comprises a housing 301. The housing 301 comprises a proximal end 302 and a distal end 303. The medicament delivery device 300 further comprises a needle 305 and a needle cover 306. The needle cover 306 is axially moveable between an extended position, similar to that shown in FIGS. 3A and 3D, and a retracted position, similar to that shown in FIGS. 3B and 3C.

In the extended position, the needle cover 306 extends from the distal end 303 of the housing 301. In the extended position, the needle cover 306 covers a distal end 307 of the needle 305. In the retracted position, the needle cover 305 is located in a proximal position relative to the extended position. In the retracted position, the needle 305 protrudes from a distal end 308 of the needle cover 306.

The medicament delivery device 300 further comprises a needle cover biasing member 311. The needle cover biasing member 311 is configured to bias the needle cover 306 in the distal direction towards the extended position.

The medicament delivery device 300 further comprises a drive mechanism 331. The drive mechanism 331 comprises a drive member 324 and a plunger rod 315. The plunger rod 315 is configured to move from a proximal position to a distal position. The drive member 324 is configured to bias the plunger rod 315 in the distal direction towards the distal position. Thus, the plunger rod 315 is configured to move from a proximal position to a distal position under the force of the drive member 324.

The medicament delivery device 300 further comprises a needle cover extension mechanism 341. The needle cover extension mechanism 341 may be a post-use mechanism. That is, the needle cover extension mechanism 341 may be operated once the medicament delivery device 300 has been used. The needle cover extension mechanism 341 comprises a second biasing member 342 and a release element 343.

The second biasing member 342 is configured to bias the needle cover into its extended position post-use of the medicament delivery device 300. The release element 343 has a first state and a second state. In the first state, the release element 343 is configured to prevent the second biasing member 342 from biasing the needle cover 306 into the extended position. In the second state, the release element 343 is configured to allow the second biasing member 342 to bias the needle cover 306 into the extended position.

One advantage of the techniques described in the present disclosure is that the biasing force of the needle cover biasing member 311 can be reduced. Thus, the force required to be applied by an operator to activate and hold the medicament delivery device 300 can be reduced. Thus, those who have difficulty with maintaining a high hold force throughout the injection duration will find using the medicament delivery device described in the present disclosure easier to hold. Furthermore, the use of the needle cover extension mechanism allows for a robust extension of the needle cover after use in order to provide protection against accidental contact with the used needle 305.

Figure 4A:
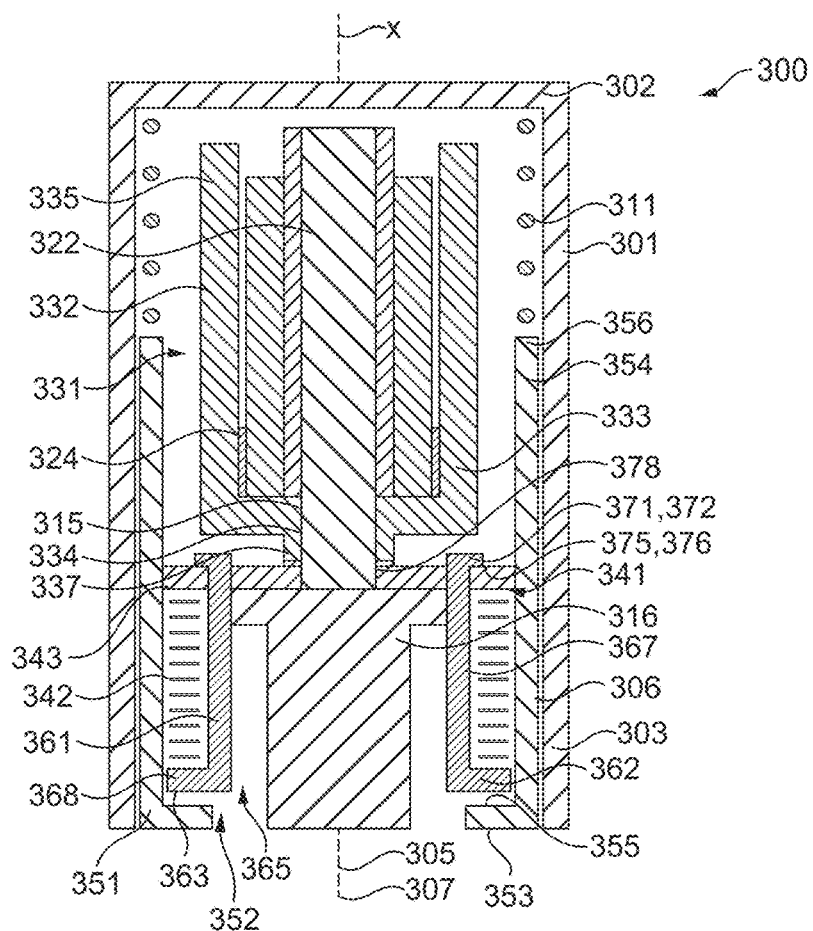
FIG. 4A shows a schematic cross-sectional side view of a medicament delivery device with its needle cover in the retracted position.
Figure 5A:
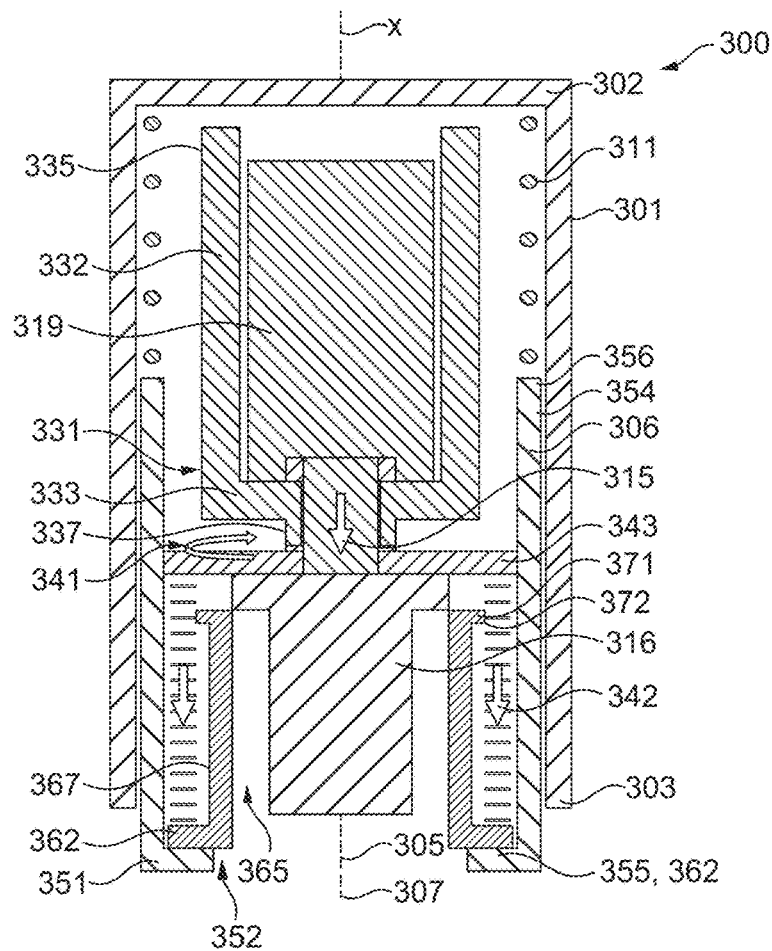
FIG. 5A shows a schematic cross-sectional side view of a medicament delivery device with its needle cover in the extended position post use.

Referring to FIG. 4A and FIG. 5A, the needle cover 306 may comprise a distal end portion 351. The distal end portion 351 of the needle cover 306 may be the distal-most portion of the needle cover 306. The distal end portion 351 may extend circumferentially about the central longitudinal axis X of the medicament delivery device 300. The distal end portion 351 of the needle cover 306 may be configured to prevent access to the needle 305 when the needle cover 306 is in the extended position. This may help prevent accidental contact with the needle 305.

The distal end portion 351 of the needle cover 306 may be annular. That is, the distal end portion 351 of the needle cover 306 may comprise an aperture 352. The aperture 352 may be located centrally in the distal end portion 351 of the needle cover 306. The aperture 352 may extend through the full thickness of the distal end portion 351 in a direction parallel to the longitudinal axis X of the medicament delivery device 300. The aperture 352 may be configured to allow the needle 305 to extend therethrough when the needle cover 306 is in the retracted position. The distal end portion 351 may also be referred to as an annular member.

The distal end portion 351 of the needle cover 306 may comprise a distally facing surface 353. The distally facing surface 353 of the needle cover 306 may be configured to be placed against an injection site.

The needle cover 306 may further comprise an arm 354. The arm 354 of the needle cover 306 may extend in the proximal direction. The arm 354 may extend proximally from the distal end portion 351 of the needle cover 306. That is, the arm 354 of the needle cover 306 may extend proximally from a proximal facing surface 355 of the distal end portion 351 of the needle cover 306. The arm 354 may extend from the periphery of the distal end portion 351 of the needle cover 306.

The arm 354 may be elongate such that the length dimension of the arm is greater than the width and thickness dimensions of the arm 354. The arm 354 may extend around only a section of the circumference of the body portion 351 of the needle cover 306, for example, but not limited to 10 to 20% of the circumference of the needle cover 306. Therefore, the arm 344 may extend arcuately around the longitudinal axis X of the medicament delivery device 100. The needle cover 306 may comprise a plurality of arms 354. The plurality of arms 354 may be spaced circumferentially about the distal end portion 351 of the needle cover 306. The plurality of arms 354 may be spaced equidistantly about the longitudinal axis X of the medicament delivery device 300. In embodiments where two arms 354 are present, the arms may be located diametrically opposite each other. In other embodiments, the needle cover 306 may comprise a single circumferentially extending arm 354.

In some embodiments, a distal end of the needle cover biasing member 311 may be mounted on a proximal end 356 of the arm 354 of the needle cover 306. A proximal end of the needle cover biasing member 311 may be mounted on a mount (not shown) on the housing 301.

The needle cover extension mechanism 341 may further comprise a second biasing member holder 361. The second biasing member holder 361 may be configured to house the second biasing member 342. The second biasing member holder 361 may be configured to hold the second biasing member 342 in a compressed state when the release element 343 is in the first state. The second biasing member holder 361 may be axially moveable within the housing 301 in the distal direction under the force of the second biasing member 342 when the release element 343 is in the second state. The second biasing member holder 361 may be rotationally locked relative to the housing 301 or another feature such as the needle cover 306.

The second biasing member holder 361 may comprise a distal end portion 362. The distal-end portion 362 of the second biasing member holder 361 may be the distal-most portion of the second biasing member holder 361. The distal end portion 362 of the second biasing member holder 361 may extend circumferentially about the central longitudinal axis X of the medicament delivery device 300. The distal end portion 362 of the second biasing member holder 361 may be configured to abut the needle cover 306 once the release element 343 has been moved to the second state. That is, when the release element 343 is in the second state, the second biasing member 342 may be configured to bias the distal end portion 362 of the second biasing member holder 361 into contact with the distal end portion 351 of the needle cover 206. A distally facing surface 363 of the distal end portion 362 of the second biasing member holder 361 may be configured to abut the proximally facing surface 355 of the distal end portion 351 of the needle cover 306.

The distal end portion 362 of the second biasing member holder 361 may be annular. That is, the distal end portion 362 of the second biasing member holder 361 may comprise an aperture 365. The aperture 365 may be located centrally in the distal end portion 362 of the second biasing member holder 361. The aperture 365 may be configured to allow the needle 305 and syringe 316 to extend therethrough.

The second biasing member holder 361 may further comprise an arm 367. The arm 367 of the second biasing member holder 361 may extend in the proximal direction. The arm 367 may extend proximally from the distal end portion 362 of the second biasing member holder 361. That is, the arm 367 of the second biasing member holder 361 may extend proximally from a proximal facing surface 368 of the distal end portion 362 of the second biasing member holder 361. The arm 367 may extend from the periphery of the aperture 365 in distal end portion 362 of the second biasing member holder 361.

The second biasing member holder 361 may further comprise a clip 371. The clip 371 may be configured to engage with the release element 343 when the release element is in the first state, as shown in FIG. 4A and FIG. 4C, and to be disengaged with the release element 343 when the release element 343 is in the second state, as shown in FIG. 5A and FIG. 5C.

The clip 371 may be located at the proximal end of the second biasing member holder 361. In some embodiments, the clip 371 may be located at the proximal end of the arm 367 of the second biasing member holder 361. In some embodiments, the clip 371 may extend in a generally perpendicular direction relative to the radius of the medicament delivery device 300. The clip 371 may be arcuate such that the clip 371 is extends perpendicular to the radius at each point along its length. In some embodiments, the clip 371 may generally extend radially outwards from the end of the arm 367. The clip 371 may comprise a distally facing surface 372. The distally facing surface 372 of the clip 371 may extend in a plane that extends perpendicularly to the longitudinal axis X of the medicament delivery device 300. The distally facing surface 372 of the clip 371 may be configured to engage with the release element 343 when the release element is in the first state, and to be disengaged with the release element 343 when the release element 343 is in the second state, as will be explained in more detail hereinafter.

Figures 4B, 4C:
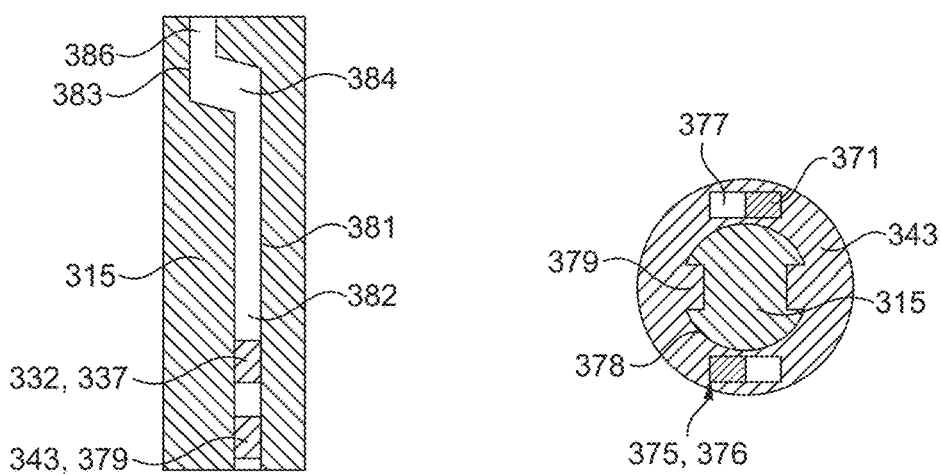
FIG. 4B shows a schematic side view of a plunger rod in a proximal position.
FIG. 4C shows a schematic top view of a needle cover extension mechanism with a release element in a first state.
Figures 5B, 5C:
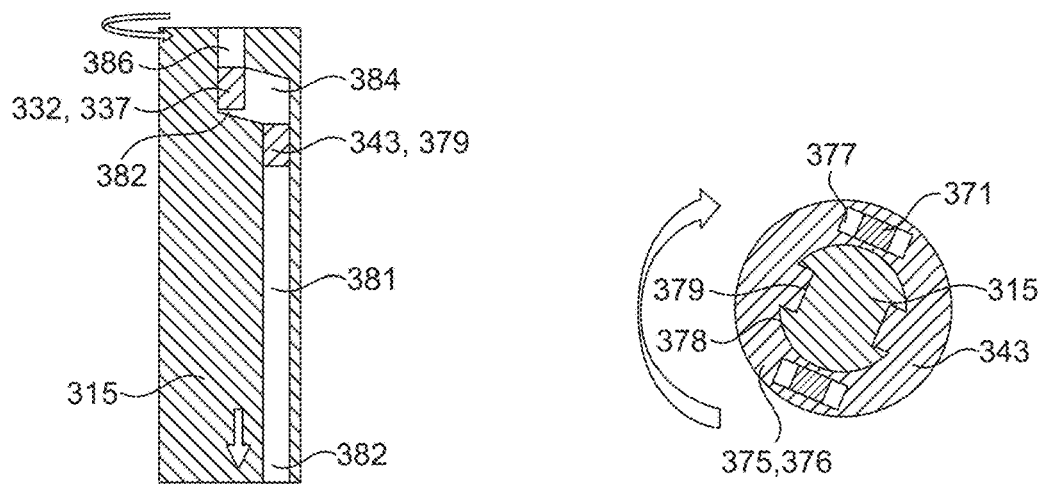
FIG. 5B shows a schematic side view of a plunger rod in a distal position.
FIG. 5C shows a schematic top view of a needle cover extension mechanism with a release element in a second state.

As shown schematically in FIGS. 4C and 5C, the release element 343 may be rotatable from the first state, shown in FIG. 4C, to the second state, shown in FIG. 5C. In some embodiments, the release element 343 may be rotatable from the first state to the second state when the plunger rod 315 is moved into the distal position, as shown in FIG. 5C. The release element 343 may be axially locked within the housing 301 of the medicament delivery device 300.

The release element 343 may comprise an engaging portion 375. The engaging portion 375 of the release element 343 may be configured to engage with the clip 371 of the second biasing member holder 361 when the release element 343 is in the first state, as shown in FIG. 4A. The engaging portion 375 of the release element 343 may be configured to be disengaged with the clip 371 of the second biasing member holder 361 when the release element 343 is in the second state, as shown in FIG. 5A. Thus, the second biasing member 342 may bias the needle cover 306 towards the extended position when the release element 343 is in the second state.

In some embodiments, the engaging portion 375 of the release element 343 may comprise a proximally facing surface 376 of the release element 343. In some embodiments, the proximally facing surface 376 may be the proximal-most surface of the release element 343. Thus, in some embodiments, the distally facing surface 372 of the clip 371 of the second biasing member holder 361 may be configured to be engaged with the proximally facing surface 376 of the release element 343 when the release element 343 is in the first state to prevent the second biasing member holder 361 from being moved in the distal direction by the second biasing member 342. In the second state, the distally facing surface 372 of the clip 371 and the proximally facing surface 376 of the release element 343 may be out of contact with each other, which allows the relative axial movement under the force of the second biasing member 342 between the second biasing member holder 361 and the release element 343.

In some embodiments, the release element 343 may comprise a slot 377, as shown in FIG. 4C and FIG. 5C. The slot 377 may extend through the thickness of the release element 343 in the longitudinal X direction of the medicament delivery device 300. The slot 377 may be configured to receive a portion of the second biasing member holder 342 when the release element 343 is in its first state. That is, the arm 367 of the second biasing member holder 361 may extend through the slot 377 when the release member 343 is in the first state such that the clip 371 is located on the proximal side of the release member 343 and distal end portion 362 of the second biasing member holder 361 is located on the distal side of the release member 343.

In some embodiments, the slot 377 may be arcuate. That is, the slot 377 may extend in the circumferential direction about the longitudinal axis X of the medicament delivery device 300. Thus, when the release element 343 is rotated from its first state to its second state, the portion of the second biasing member holder 342 extending through the slot 377 does not inhibit movement from the first state to the second state. In some embodiments, the width of the slot 377, i.e. dimension in the radial direction, may increase in the circumferential direction. That is, one circumferential end of the slot 377 may be wider than the other circumferential end of the slot 377.

It will be appreciated that in some embodiments, the second biasing member holder 342 may comprise a plurality of clips 371 and the release element 343 may comprise a corresponding number of slots 377.

The release member 343 may comprise a flat plate 343. In some embodiments, the flat plate 343 may be generally circular. Thus, the flat plate 343 may also be referred to herein as a disc 343. However, it will be appreciated that the flat plate 343 may have any suitable shape.

In some embodiments, the release member 343 may be annular. That is, the release member 343 may be a disc having an aperture 378. The aperture 378 may be located centrally in the release member 343. The aperture 378 may extend fully through the thickness of the release member 343 in a direction parallel to the longitudinal axis X of the medicament delivery device 300. The aperture 378 may be configured to allow the plunger rod 315 to extend therethrough.

In some embodiments, the release member 343 may be rotationally coupled to the plunger rod 315, as shown schematically in FIGS. 4B, 4C, 5B, and 5C. The release member 343 may comprise a protrusion 369, shown in FIGS. 4C and 5C. The protrusion 369 may be configured to engage with a feature of the plunger rod 315, as will be explained in more detail hereinafter. The protrusion 369 of the release member 343 may extend radially from an inner periphery of the release member 343. That is, the protrusion 369 may extend radially inwards into the aperture 378.

As shown in FIGS. 4A and 5A, the second biasing member 342 may be located between the release element 343 and the second biasing member holder 361. The second biasing member 342 may extend between and act upon the distal surface of the release element 343 and the proximally facing surface 368 of the distal end portion 362 of the second biasing member holder 361.

When the release member 343 is in the first state, the clip 371 of the second biasing member holder 361 may be engaged with the release element 343 to prevent relevant axial movement therebetween. Therefore, when the release element 343 is in the first state, the second biasing member 342 may be held in its compressed state by the second biasing member holder 361, as shown in FIG. 4A. When the release member 343 is in the second state, the clip 371 of the second biasing member holder 361 may be disengaged with the release element 343 to allow relevant axial movement therebetween. Therefore, when the release element 343 is in the second state, the second biasing member 342 may extend distally, as shown in FIG. 5A.

The second biasing member 342 may be configured to bias the second biasing member holder 361 into contact with the needle cover 306 to bias the needle cover into the extended position when the release element 343 is in the second state. That is, when the clip 371 of the second biasing member holder 361 aligns with the slot 377 in the release member 343, the second biasing member 342 may extend. In some embodiments, the distal end portion 362 of the second biasing member holder 361 may be biased into contact with the distal end portion 351 of the needle cover 306 by the second biasing member 342 in order to bias the needle cover 306 towards the extended position, as shown in FIG. 5A.

In some embodiments, the needle cover biasing member 111 and/or the second biasing member 342 may be form be a coil spring.

Referring to FIG. 4B and FIG. 5B, a schematic cross-sectional side view of the plunger rod 315 is shown. The plunger rod 315 may be generally cylindrical. The plunger rod 315 may be rotatable between a first rotational position, shown in FIGS. 4B and 4C, and a second rotational position, shown in FIGS. 5B and 5C. The plunger rod 315 may be rotated into the second rotational position when the plunger rod 315 is moved to its distal position. It will be appreciated that the movement of the plunger rod 315 from its first rotational position to its second rotational position may begin immediately prior to the plunger rod 315 reaching its distal position.

Due to the release element 343 being rotationally coupled to the plunger rod 315, rotation of the plunger rod 315 from the first rotational position to the second rotational position may cause the release element 343 to also rotate. The rotation of the release element 343 may rotate the slot 377 of the release member 343 relative to the clip 371 of the second biasing member holder 361. Thus, in the first rotational position of the plunger rod 315, the release element 343 may be in its first state in which the release element 343 engages with the clip 371 of the second biasing member holder 361 to prevent the second biasing member 342 from biasing the needle cover 306 into the extended position. However, in the second rotational position of the plunger rod 315, the release element 343 is rotated to its second state in which the slot 377 of the release member 343 aligns with the clip 371 of the second biasing member holder 342. Therefore, the second biasing member 342 is released and can extend distally to bias the needle cover 306 towards the extended position.

As shown in FIG. 4B and FIG. 5B, the plunger rod 315 may comprise a slot 381. The slot 381 may be formed in the outer circumferential surface of the plunger rod 315. The slot 381 may extend generally longitudinally. The slot 381 may extend generally along at least a majority of the length of the plunger rod 315. In some embodiments, the slot 381 may extend substantially the whole length of the plunger rod 315.

The slot 381 may comprise a first portion 382. The first portion 382 of the slot 381 may extend longitudinally. The first portion 382 of the slot 381 may extend from the distal end of the plunger rod 315 in a proximal direction. The slot 381 may further comprise a second portion 383. The second portion 383 of the slot 381 may extend longitudinally. The second portion 383 of the slot 381 may extend from the proximal end of the plunger rod 315 in a distal direction. The second portion 383 of the slot 381 may be offset from the first portion 382 of the slot 381. That is, the second portion 383 of the slot 381 may be circumferentially spaced from the first portion 382 of the slot 381. In some embodiments, the first and second portions 382, 383 of the slot 381 may overlap in the axial direction whilst being circumferentially spaced.

The slot 381 may further comprise a third portion 384. The third portion 384 of the slot 381 may connect the first and second portions 382, 383 of the slot 381. That is, the third portion 384 of the slot 381 may connect the proximal end of the first slot 382 to the distal end of the second slot 383. The third portion 384 of the slot 381 may extend at an inclined angle to the longitudinal axis X of the medicament delivery device 300 in a circumferential direction. That is, the third portion 384 of the slot 381 may extend helically about the outer surface of the plunger rod 315.

The protrusion 379 of the release element 343 may be located in the slot 381 of the plunger rod 315, as shown in FIGS. 4C and 4D, and schematically represented in FIGS. 5B and 5C. The protrusion 379 of the release element 343 and the slot 381 of the plunger rod 315 may be configured to rotationally couple the release element 343 and the plunger rod 315. The protrusion 379 of the release element 343 and the slot 381 of the plunger rod 315 may be configured to allow axial relative movement between the plunger rod 315 and the release element 343.

The protrusion 379 of the release element 343 may be located in the first portion 382 of the slot 381 in the plunger rod 315. The length of the first portion 382 of the slot 381 in the plunger rod 315 may be at least as long as the stroke length of the plunger rod 315 from its proximal position to its distal position.

As shown in FIG. 4B, the protrusion 379 of the release element 343 may be located in the first portion 382 of the slot 381 in the plunger rod 315 when the plunger rod 315 is in its proximal position. That is, the protrusion 379 of the release element 343 may be located in the distal end of the first portion 382 of the slot 381 in the plunger rod 315 when the plunger rod 315 is in the proximal position. As shown in FIG. 5B, the protrusion 379 of the release element 343 may be located in the first portion 382 of the slot 381 in the plunger rod 315 when the plunger rod 315 is in its distal position. That is, the protrusion 379 of the release element 343 may be located in the proximal end of the first portion 382 of the slot 381 in the plunger rod 315 when the plunger rod 315 is in the distal position. By maintaining the protrusion 379 in the first portion 382 of the slot 381 in the plunger rod 315, the release element 343 and be kept rotationally coupled to the plunger rod 315.

Referring to FIG. 4A and FIG. 5A, the drive mechanism 331 may further comprise a drive member housing 332. The drive member housing 332 may be configured to at least partially house the drive member 224 of the drive mechanism 331. The drive member housing 332 may be located proximally of the release member 343. The drive member housing 332 may be located proximate to the proximal end 302 of the housing 301. The drive member housing 332 may be rotationally fixed within the housing 301. In some embodiments, the drive member housing 332 may be axially fixed within the housing 301.

The drive member housing 332 may be generally cylindrical. The drive member housing 332 may comprise a distal end portion 333. The distal end portion 333 may extend perpendicularly to the longitudinal axis X of the medicament delivery device 300. The distal end portion 333 of the drive member housing 332 may extend circumferentially around the central longitudinal axis X of the medicament delivery device 300.

The distal end portion 333 of the drive member housing 332 may be annular. That is, the distal end portion 333 of the drive member housing 332 may comprise an aperture 334. The aperture 334 may be located centrally in the distal end portion 333 of the drive member housing 332. The aperture 334 may extend through the full thickness of the distal end portion 333 of the drive member housing 332 in a direction parallel to the longitudinal axis X of the medicament delivery device 300. The aperture 334 may be configured to allow the plunger rod 315 to move axially therethrough.

The drive member housing 332 may further comprise a side wall 335. The side wall 335 may be a circumferentially extending wall 335. The circumferentially extending side wall 335 may extend from a proximally facing surface of the distal end portion 333 in the proximal direction. The circumferentially extending side wall 335 may extend from an outer periphery of the proximally facing surface of the distal end portion 333.

The drive member housing 332 may further comprise a projection 337. The projection 337 may be configured to be located in the slot 381 of the plunger rod 315. In some embodiments, the projection 337 may extend radially from an inner periphery of the drive member housing 332. The projections 337 may extend radially inwards into the aperture 334 in the distal end portion 333 of the drive member housing 332.

As shown in FIG. 4A and schematically in FIG. 4B, the projection 337 of the drive member housing 332 may be located in the slot 381 of the plunger rod 315. The projection 337 of the drive member housing 332 may be located in the slot 381 proximally relative to the location of the protrusion 379 in the slot 381 of the plunger rod 315. The projection 337 and slot 381 may be configured to allow axial relative movement between the plunger rod 315 and the drive member housing 332. Due to the geometry of the slot 381 in the plunger rod 315, the projection 337 and slot 381 may also be configured to cause the plunger rod 315 to move into its second rotational position as the plunger rod reaches its distal position.

As shown in FIG. 4B, the projection 337 of the drive member housing 332 may be located in the first portion 382 of the slot 381 in the plunger rod 315 when the plunger rod 315 is in its proximal position. The projection 337 may be located in the first portion 382 of the slot 381 for the majority of the plunger rod 315 stroke from the proximal position to the distal position. As shown in FIG. 5B, the projection 337 of the drive member housing 332 may be located in the second portion 383 of the slot 381 in the plunger rod 315 when the plunger rod 315 is in its distal position. As a result, the plunger rod 315 is rotated from its first rotational position to its second rotational position and moves the release element 343 from its first state to its second state as previously described.

As the plunger rod 315 approaches the end of its stroke, i.e. as the plunger approaches the distal position, the projection 337 of the drive member housing 332 reaches the end of the first portion 382 of the slot 381 and abuts the inclined surface of the third connecting portion 384 of the slot 381. Due to the inclination of the helically extending third portion 384 of the slot 381, the plunger rod 315 can still be moved distally relative to the drive member housing 332 and is additionally caused to rotate by the projection 337 in the third portion 384 of the slot 381. The rotational and axial motion of the plunger rod 315 continues until the projection 337 of the drive member housing 332 reaches the second portion 383 of the slot 381.

In some embodiments, the second portion 383 of the slot may comprise a narrow section 386. The narrow section 386 of the slot 381 may be narrower than the first portion 382 of the slot 381. The narrow section 386 of the second portion 383 of the slot 381 may be narrower than the width of the projection 337 of the drive member housing 332. Therefore, the narrow section 386 may act as a stop to prevent further distal movement of the plunger rod 315. Alternatively, the second portion 383 of the slot 381 may end before the proximal end of the plunger rod 315, thus providing a stop.

Referring to FIG. 4A and FIG. 5A, the drive mechanism 331 may further comprise a collar 319. The collar 319 may be at least partially located in the drive member housing 332. The collar 319 may be axially fixed relative to the drive member housing 332. The collar 319 may be configured to rotate. The rotating collar 319 may comprise a screw thread 322. The screw thread 322 may form a threaded surface of the collar 319. The threaded surface may be an inner surface of the collar 319. As shown in FIG. 4A, the plunger rod 315 may also comprise a screw thread 322. That is, the outer surface of the plunger rod 315 may comprise a screw thread 322. The threaded surface 322 of the collar 319 and the threaded surface 322 of the plunger rod 315 may be configured to cooperate.

When the drive member 224 is actuated, the drive member 224 may be configured to rotate the collar 319. Cooperation between the threaded surfaces 322 on the collar 319 and the plunger rod 315 may transform the rotational motion of the collar 319 into axial displacement of the plunger rod 315 in the distal direction. Movement of the plunger rod 315 in relation to the drive member housing 332 may be as described above.

In some embodiments, the drive member 224 may comprise a torsional spring.

The medicament delivery device 300 may further comprise a needle cover lock 345. The needle cover lock 345 may be configured to prevent proximal movement of the needle cover 306 once the needle cover 306 is in the extended position post-use.

Although described previously in detail, a brief description of the method of moving a needle cover 306 to its extended position after use will be given. The method comprises moving a plunger rod 315 from a first rotational position to a second rotational position to move a release element 343 from a first state, in which the release element 343 prevents extension of a second biasing member 342, to a second state, in which the release element 343 allows extension of a second biasing member 342. The method further comprises moving the needle cover 306 under the biasing force of the second biasing member 342 from the retracted position, in which a distal end of a needle 305 protrudes from a distal end 308 of the needle cover 306, to an extended position, in which the needle cover 306 covers the distal end 307 of the needle 305.

In some embodiments, the medicament delivery devices described herein may be configured to inject greater than 2 ml of medicament. In some embodiments, the medicament delivery devices described herein may be configured to inject medicament having a viscosity of greater than 25 cP.

The features described and/or contemplated in relation to the medicament delivery device 200 may be incorporated in another medicament delivery device, for example a medicament delivery device having a different mechanism for dispensing medicament to that described in relation to the medicament delivery device 100, and/or a medicament delivery device which is configured to inject 2 ml or less of medicament and/or a medicament delivery device which is configured to inject medicament having a viscosity of 25 cP or less, and/or a medicament delivery device in which the medicament is contained in a cartridge which is initially separated from the needle when the needle cover is in the initial position.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N—(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a caperturesterol-reducing antisense therapeutic for the treatment of familial hyper-caperturesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

REFERENCE NUMERALS

10 Drug Delivery Device
11 Housing
12 Cap Assembly
13 Needle Sleeve
17 Needle
20 Distal Region
22 Button
23 Piston
100 Medicament Delivery Device
101 Housing
102 Proximal End
103 Distal End
105 Needle
106 Needle Cover
107 Distal End
108 Distal End
111 Needle Cover Biasing Member
115 Plunger Rod
116 Syringe
117 Piston
119 Collar
122 Screw Thread
124 Drive Member
125 Injection Site
200 Medicament Delivery Device
201 Housing
202 Proximal End
203 Distal End
205 Needle
206 Needle Cover
207 Distal End
208 Distal End
211 Needle Cover Biasing Member
215 Plunger Rod 224 Drive Member
225 Injection Site
231 Drive Mechanism
241 Needle Cover Extension Mechanism
242 Second Biasing Member
243 Release Element
245 Needle Cover Lock
300 Medicament Delivery Device
301 Housing
302 Proximal End
303 Distal End
305 Needle
306 Needle Cover
307 Distal End
308 Distal End
311 Needle Cover Biasing Member
315 Plunger Rod
316 Syringe
319 Collar
332 Screw Thread
324 Drive Member
331 Drive Mechanism
332 Drive Member Housing
333 Distal End Portion
334 Aperture
335 Side Wall
337 Projection
341 Needle Cover Extension Mechanism
342 Second Biasing Member
343 Release Element
345 Needle Cover Lock
351 Distal End Portion
352 Aperture
354 Arm
361 Second Biasing Member Holder
362 Distal End Portion
363 Distally Facing Surface
365 Aperture
367 Arm
368 Proximally Facing Surface
371 Clip
372 Distally Facing Surface
375 Engaging Portion
376 Proximally Facing Surface
377 Slot
378 Aperture
379 Protrusion
381 Slot
382 First Portion
383 Second Portion
384 Third Portion
386 Narrow Section

The invention claimed is:

1. A medicament delivery device comprising:
a housing comprising a proximal end and a distal end;
a needle and a needle cover,
   wherein the needle cover is axially movable between an extended position, in which the needle cover extends from the distal end of the housing and covers a distal end of the needle, and a retracted position, in which the needle cover is located in a position proximal to the extended position such that the needle protrudes from a distal end of the needle cover;
a needle cover biasing member configured to bias the needle cover axially in a distal direction towards the extended position;
a drive mechanism comprising a drive member, and a plunger rod configured to move from a proximal position to a distal position under the force of the drive member; and
a needle cover extension mechanism comprising
   a second biasing member configured to bias the needle cover into the extended position post-use of the medicament delivery device,
   a release element having a first state configured to prevent the second biasing member from biasing the needle cover into the extended position and a second state configured to allow the second biasing member to bias the needle cover into the extended position, wherein the release element is in the second state when the plunger rod is in the distal position, and
   a second biasing member holder, wherein the release element comprises an engaging portion, wherein the second biasing member holder comprises a clip configured to engage with the engaging portion of the release element when the release element is in the first state and to be disengaged with the engaging portion of the release element when the release element is in the second state.

2. The medicament delivery device according to claim 1, wherein the release element is rotatable from the first state to the second state when the plunger rod is moved into the distal position.

3. The medicament delivery device according to claim 1, wherein the release element comprises a slot through which the second biasing member holder extends in the first state, the release element being configured to rotate relative to the second biasing member holder such that when the release element is in the first state an engaging surface of the clip engages with a proximal engaging surface of the release element and when the release element is in the second state the engaging surface of the clip is disengaged from the proximal engaging surface of the release element.

4. The medicament delivery device according to claim 3, wherein the slot extends arcuately in the release element.

5. The medicament delivery device according to claim 3, wherein the second biasing member is located between a distal surface of the release element and a proximal facing surface of the second biasing member holder, the second biasing member being configured to bias the second biasing member into contact with the needle cover to bias the needle cover into the extended position when the engaging surface of the clip aligns with the slot in the release element in the second state.

6. The medicament delivery device according to claim 5, wherein a distal end portion of the second biasing member holder is configured to abut a distal end portion of the needle cover when the release element is in the second state and the second biasing member extends distally.

7. The medicament delivery device according to claim 1, wherein the release element comprises an annular flat plate.

8. The medicament delivery device according to claim 1, wherein at least one of the needle cover biasing member and the second biasing member is a coil spring.

9. The medicament delivery device according to claim 1, wherein the release element is rotationally coupled to the plunger rod, and wherein the plunger rod is rotatable between a first rotational position and a second rotational position when the plunger rod is in the distal position to move the release element from the first state into the second state.

10. The medicament delivery device according to claim 9, wherein the plunger rod comprises a slot having a first portion extending longitudinally, and wherein the release element comprises a protrusion located in the slot, the slot and protrusion being configured to allow relative axial movement between the plunger rod and the release element.

11. The medicament delivery device according to claim 10, wherein the protrusion of the release element is located in the first portion of the slot when the plunger rod is in the proximal position and when the plunger rod is in the distal position.

12. The medicament delivery device according to claim 10, wherein the drive mechanism further comprises a drive member housing, the drive member housing comprising a projection located in the slot of the plunger rod, wherein the projection is located in the first portion of the slot for the majority of a plunger rod stroke from the proximal position such that the plunger rod is maintained in the first rotational position, and wherein the projection is located in a second offset portion of the slot when the plunger rod is in the distal position such that the plunger rod is moved to the second rotational position.

13. The medicament delivery device according to claim 12, wherein the first portion and the second offset portion of the slot are connected by a third portion of the slot that extends helically about the plunger rod, wherein engagement between the projection of the drive member housing and the third portion of the slot induces the plunger rod to rotate from the first rotational position to the second rotational position as the plunger rod is moved axially into the distal position.

14. The medicament delivery device according to claim 12, wherein the projection of the drive member housing is located proximally to the protrusion of the release element.

15. The medicament delivery device according to claim 12, wherein the drive mechanism further comprises a rotating collar located at least partially within the drive member housing, the rotating collar comprising a threaded surface, wherein the plunger rod comprises a threaded surface configured to cooperate with the threaded surface of the rotating collar, and wherein the drive member comprises a torsion spring.

16. The medicament delivery device according to claim 1, wherein the medicament delivery device is configured to inject greater than 2 ml of a medicament and/or wherein the medicament delivery device is configured to inject a medicament having a viscosity of greater than 25 cP.

17. The medicament delivery device according to claim 1, further comprising a needle cover lock configured to prevent proximal movement of the needle cover once the needle cover is in the extended position post-use.

18. The medicament delivery device according to claim 1, wherein the medicament delivery device comprises a medicament.

19. A method of moving a needle cover of a medicament delivery device to an extended position after use,
wherein the medicament delivery device comprises:
a housing comprising a proximal end and a distal end,
a needle,
a needle cover,
a drive mechanism,
a needle cover extension mechanism, and
a needle cover biasing member configured to bias the needle cover axially in a distal direction towards the extended position of the needle cover,
wherein the method comprises:
moving a plunger rod of the drive mechanism, the plunger rod being rotationally coupled with a release element, from a first rotational position to a second rotational position to move the release element from a first state, in which the release element prevents extension of a second biasing member of the needle cover extension mechanism, to a second state, in which the release element allows extension of the second biasing member, the second biasing member being configured to bias the needle cover into the extended position post-use of the medicament delivery device, and
moving the needle cover under the biasing force of the second biasing member from a retracted position, in which the needle cover is located in a position proximal to the extended position such that a needle protrudes from a distal end of the needle cover, to the extended position, in which the needle cover extends from a distal end of the housing and covers the distal end of the needle.

20. A medicament delivery device comprising:
a housing comprising a proximal end and a distal end;
a needle and a needle cover,
wherein the needle cover is axially movable between an extended position, in which the needle cover extends from the distal end of the housing and covers a distal end of the needle, and a retracted position, in which the needle cover is located in a position proximal to the extended position such that the needle protrudes from a distal end of the needle cover;
a needle cover biasing member configured to bias the needle cover axially in a distal direction towards the extended position;
a drive mechanism comprising a drive member and a plunger rod, the plunger rod being configured to move from a proximal position to a distal position under the force of the drive member; and
a needle cover extension mechanism comprising:
a second biasing member configured to bias the needle cover into the extended position post-use of the medicament delivery device, and
a release element having a first state configured to prevent the second biasing member from biasing the needle cover into the extended position and a second state configured to allow the second biasing member to bias the needle cover into the extended position,
wherein the release element is in the second state when the plunger rod is in the distal position, wherein the release element is rotationally coupled to the plunger rod, and wherein the plunger rod is rotatable between a first rotational position and a second rotational position when the plunger rod is in the distal position to move the release element from the first state into the second state.

* * * * *